United States Patent
Park et al.

(10) Patent No.: US 7,816,671 B2
(45) Date of Patent: Oct. 19, 2010

(54) ORGANIC THIN FILM TRANSISTOR COMPRISING PHOSPHATE-BASED SELF-ASSEMBLED MONOLAYER AND METHOD OF MANUFACTURING THE SAME

(75) Inventors: Jeong Il Park, Yongin-si (KR); Jung Seok Han, Yongin-si (KR); Sang Yoon Lee, Yongin-si (KR); Eun Jeong Jeong, Yongin-si (KR); Kook Min Han, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 698 days.

(21) Appl. No.: 11/703,247

(22) Filed: Feb. 7, 2007

(65) Prior Publication Data

US 2008/0067504 A1    Mar. 20, 2008

(30) Foreign Application Priority Data

Sep. 19, 2006  (KR)  .................. 10-2006-0090596

(51) Int. Cl.
*H01L 51/10* (2006.01)
(52) U.S. Cl. ........... 257/40; 257/E51.006; 257/E51.052
(58) Field of Classification Search .................. 257/40, 257/E51.001–E51.052; 438/99
See application file for complete search history.

(56) References Cited

U.S. PATENT DOCUMENTS

| | | | |
|---|---|---|---|
| 6,433,359 B1 * | 8/2002 | Kelley et al. ................... 257/40 |
| 6,646,285 B1 * | 11/2003 | Kagan et al. ................... 257/40 |
| 7,208,782 B2 * | 4/2007 | Klauk et al. ................. 257/225 |
| 2002/0045289 A1 * | 4/2002 | Dimitrakopoulos et al. ... 438/99 |
| 2004/0185600 A1 * | 9/2004 | Kagan et al. ................... 438/99 |
| 2006/0226441 A1 * | 10/2006 | Seo et al. ..................... 257/190 |
| 2006/0289858 A1 * | 12/2006 | Park et al. ..................... 257/40 |
| 2007/0063195 A1 * | 3/2007 | Kim et al. ..................... 257/40 |

OTHER PUBLICATIONS

Kelley, T.W., et al. "High-Performance OTFTs Using Surface-Modified Alumina Dielectrics." J. Phys. Chem. B, vol. 107 (2003): pp. 5877-5881.*

Hoque, E., et al. "Phosphonate Self-Assembled Monolayers on Aluminum Surfaces." J. Chem. Phys., vol. 124 (2006): Article 174710.*

Hoque, E., et al. "Phosphonate Self-Assembled Monolayers on Aluminum Surfaces." J. Chem. Phys., vol. 124 (2006): Article 174710.*

Jaehne, E., et al. "Synthesis of Adhesion Promoters for Grafting Polythiophene onto Metal Oxides." Designed Mono. & Poly., vol. 5, No. 4 (2002): pp. 427-443.*

(Continued)

*Primary Examiner*—Matthew W Such
(74) *Attorney, Agent, or Firm*—Harness, Dickey & Pierce, P.L.C.

(57) ABSTRACT

Disclosed is an organic thin film transistor including a phosphate-based self-assembled monolayer and a method of manufacturing the same. Example embodiments relate to an organic thin film transistor, which may include a single bond type phosphate-based self-assembled monolayer without intermolecular cross-linking, between source/drain electrodes and an organic semiconductor layer, thus exhibiting improved electrical properties, e.g., increased charge mobility, and to a method of manufacturing the organic thin film transistor.

9 Claims, 3 Drawing Sheets

OTHER PUBLICATIONS

Gardner, T.J., et al. "Systems for Orthogonal Self-Assembly of Electroactive Monolayers on Au and Ito: An Approach to Molecular Electronics." J. Am. Chem. Soc., vol. 117 (1995): pp. 6927-6933.*

Appleyard, S.F.J., et al. "Organic Electroluminescent Devices: Enhanced Carrier Injection Using SAM Derivatized Ito Electrodes." J. Mater. Chem., vol. 10 (2000): pp. 169-173.*

* cited by examiner

US 7,816,671 B2

ORGANIC THIN FILM TRANSISTOR COMPRISING PHOSPHATE-BASED SELF-ASSEMBLED MONOLAYER AND METHOD OF MANUFACTURING THE SAME

PRIORITY STATEMENT

This non-provisional application claims priority under 35 U.S.C. §119 to Korean Patent Application No. 2006-0090596, filed on Sep. 19, 2006, in the Korean Intellectual Property Office (KIPO), the entire contents of which are herein incorporated by reference.

BACKGROUND

1. Field

Example embodiments relate to an organic thin film transistor (OTFT) including a phosphate-based self-assembled monolayer and a method of manufacturing the same. Other example embodiments relate to an OTFT, which may include a single bond type phosphate-based self-assembled monolayer without intermolecular crosslinking, between source/drain electrodes and an organic semiconductor layer, thus exhibiting improved electrical properties, e.g., increased charge mobility, and to a method of manufacturing the same.

2. Description of the Related Art

After the development of polyacetylene, which is a conjugated organic polymer having semiconductor properties, organic semiconductors are receiving attention as a novel electrical and electronic material thanks to the advantages of organic material, for example, various synthesis methods, easier formability into fibers or films, flexibility, conductivity, and decreased preparation costs, and thus has been intensively and extensively studied in the wide field of functional electronic devices and optical devices.

Among devices using such a conductive polymer, research into OTFTs including a semiconductor layer formed of organic material is being conducted all over the world. Compared to conventional silicon thin film transistors, OTFTs may be advantageous because a semiconductor layer may be formed through an atmospheric pressure printing process in place of plasma-enhanced chemical vapor deposition (PECVD), and all of the fabrication processes may be carried out using a roll-to-roll process on a plastic substrate, if necessary, thus decreasing the cost of fabricating the transistor. Accordingly, the OTFT may be variously applicable to devices for driving active displays, smart cards and/or plastic chips for inventory tags.

However, the OTFT may have lower charge mobility and higher operating voltage and threshold voltage than conventional silicon thin film transistors. For example, where an OTFT having a bottom contact structure or a top gate structure, adhesion between material for source/drain electrodes and organic semiconductor material for a semiconductor layer may be undesirable due to the different surface properties thereof, and also the electrode material may have a lower work function than the organic semiconductor material, thereby forming a Schottky barrier between the semiconductor layer and the source/drain electrodes, resulting in a lower charge mobility.

In order to solve the problems, methods of surface treating the interface of the semiconductor layer and the source/drain electrodes with a self-assembled monolayer (SAM) compound have been employed. As such, the conventional SAM compound may be known to be phosphates, silanes, or thiols. Among these compounds, a phosphate-based SAM compound may be known to be a material having a dichlorophosphate functional group. Although the dichlorophosphate functional group is advantageous because it may have higher reactivity and thus may easily form the SAM on a substrate, it may be very sensitive to moisture and may be easily deformed, undesirably lowering stability.

Therefore, recently, research has been directed to the development of a novel and more stable SAM for use in surface treatment of source/drain electrodes.

SUMMARY

Accordingly, example embodiments have been made keeping in mind the above problems occurring in the related art, and example embodiments provide an OTFT, which may include a more stable phosphate-based SAM having increased reactivity between source/drain electrodes and an organic semiconductor layer, thus improving electrical properties, for example, charge mobility. Example embodiments provide a method of manufacturing such an OTFT. Example embodiments provide an OTFT, including a substrate, a gate electrode, a gate insulating layer, source/drain electrodes, an organic semiconductor layer, and a single bond type phosphate-based SAM without intermolecular crosslinking. For example, the OTFT of example embodiments may have a bottom contact structure or a top gate structure.

Example embodiments provide a method of manufacturing an OTFT, including forming a gate electrode on a substrate, forming a gate insulating layer on the gate electrode, forming source/drain electrodes on the gate insulating layer, forming a single bond type phosphate-based SAM without intermolecular crosslinking, on the source/drain electrodes, and forming an organic semiconductor layer on the SAM and the gate insulating layer.

In addition, example embodiments provide a method of manufacturing an OTFT, including forming source/drain electrodes on a substrate, forming a single bond type phosphate-based SAM without intermolecular crosslinking, on the source/drain electrodes, forming an organic semiconductor layer on the SAM and the substrate, forming a gate insulating layer on the organic semiconductor layer, and forming a gate electrode on the gate insulating layer.

Also, the method of example embodiments may further include subjecting the surface of the source/drain electrodes to acid treatment or UV-ozone treatment, between forming source/drain electrodes on the gate insulating layer and forming a single bond type phosphate-based SAM without intermolecular crosslinking, on the source/drain electrodes or between forming source/drain electrodes on a substrate and forming a single bond type phosphate-based SAM without intermolecular crosslinking, on the source/drain electrodes.

BRIEF DESCRIPTION OF THE DRAWINGS

Example embodiments will be more clearly understood from the following detailed description taken in conjunction with the accompanying drawings.

FIG. 1 is a schematic view illustrating a mechanism for forming an SAM, which is included in an OTFT of example embodiments;

FIG. 2 is a schematic sectional view illustrating a bottom contact type OTFT, according to example embodiments;

FIG. 3 is a schematic sectional view illustrating a top gate type OTFT, according to example embodiments; and FIG. 4 is a graph illustrating a current transfer curve of the OTFTs of Example 6 and Comparative Example 2.

Figure 1:
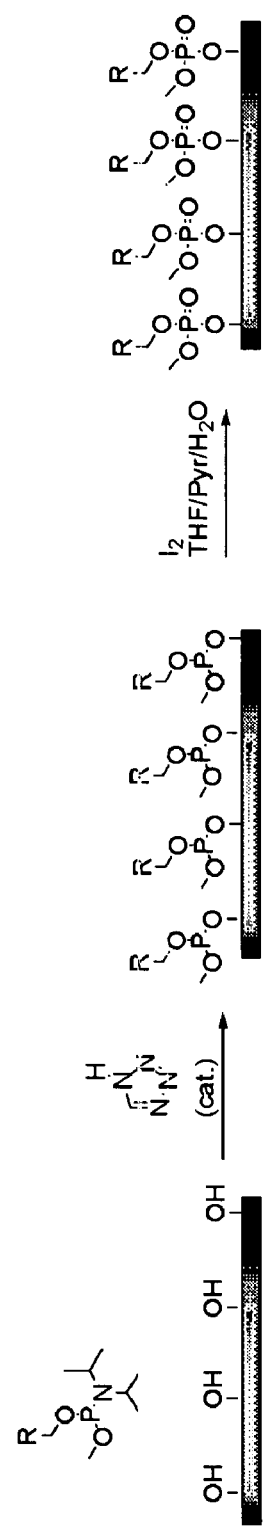
FIGS. 1-4 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. In particular, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, a detailed description will be given of example embodiments with reference to the appended drawings. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to example embodiments, the OTFT, including a substrate, a gate electrode, a gate insulating layer, source/drain electrodes, an organic semiconductor layer, and a single bond type phosphate-based SAM without intermolecular crosslinking, may be provided.

In example embodiments, the term "single bond type phosphate-based SAM without intermolecular crosslinking" indicates an SAM in which individual molecules constituting the monolayer are not crosslinked with each other but form single bonds with a functional group exposed to the surface of the source/drain electrodes at a ratio of about 1:1, and which may have a phosphate ($PO_4$) group as a binding group, for example, a functional group, to the surface of the electrode.

The SAM of example embodiments may have a specific mechanism in which phosphate functional groups contained in individual molecules constituting the SAM are not crosslinked with each other but form single bonds with functional groups, e.g., —OH, exposed to the surface of the source/drain electrodes at a ratio of about 1:1 to thus form an SAM. FIG. 1 schematically illustrates the mechanism for forming the SAM according to example embodiments.

In example embodiments, the phosphate-based SAM having a specific mechanism may be provided between the source/drain electrodes and the organic semiconductor layer to thus modify the surface of the source/drain electrodes. Thereby, contact resistance between the source/drain electrodes and the organic semiconductor layer may be decreased and electron injection performance may be enhanced, therefore improving the electrical properties of the OTFT, including charge mobility.

For example, the phosphate-based SAM of example embodiments may be formed from a precursor compound represented by Formula 1 or 2 below, but example embodiments may not be limited thereto:

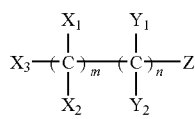

Formula 1 wherein Z is $OPN(R_2)_2OR_1$, in which $R_1$ and $R_2$ are each independently a $C_{1-30}$ alkyl group, $R_1$ and $R_2$ being substitutable with one or more selected from among a cyano group, an alkoxy group, and a $C_{6-12}$ aryl group, $X_1$, $X_2$, $X_3$, $Y_1$ and $Y_2$ are each independently hydrogen, fluorine, a $C_{1-12}$ alkyl group, a $C_{6-30}$ aromatic group, or a $C_{2-30}$ heteroaromatic group containing one or more heterogeneous atoms, the aromatic group or heteroaromatic group being substitutable with one or more selected from among a $C_{1-12}$ alkyl group, an alkoxy group, an ester group, a carboxyl group, a thiol group, and an amine group, and m is an integer from about 0 to about 50, and n is an integer from about 1 to about 50; and

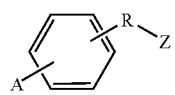

Formula 2 wherein Z is $OPN(R_2)_2OR_1$, in which $R_1$ and $R_2$ are each independently a $C_{1-30}$ alkyl group, $R_1$ and $R_2$ being substitutable with one or more selected from among a cyano group, an alkoxy group, and a $C_{6-12}$ aryl group, A is hydrogen, fluorine, an alkoxy group, a $C_{6-30}$ aromatic group, or a $C_{2-30}$ heteroaromatic group containing one or more heterogeneous atoms, the aromatic group or heteroaromatic group being substitutable with one or more selected from among a $C_{1-12}$ alkyl group, an alkoxy group, an ester group, a carboxyl group, a thiol group, and an amine group, and the $C_{1-12}$ alkyl group being substitutable with one or more selected from among fluorine, an alkoxy group, an ester group, a carboxyl group, a thiol group, and an amine group, and R is a $C_{1-30}$ alkyl group, which is substitutable with one or more selected from among an alkoxy group, and a $C_{6-12}$ aryl group.

For example, the SAM of example embodiments may be formed from a precursor compound including phosphoramidite as a group for binding to the surface of the electrode and a hydrocarbon group as a tail part.

As such, in Formulas 1 and 2, at least one among $X_1$, $X_2$, $X_3$, $Y_1$ and $Y_2$ may be substituted with one or more fluorine atoms, and A may also be substituted with one or more fluorine atoms.

Although the exact mechanism has not been found, when the SAM is formed with a precursor compound containing fluorine, the fluorine in the SAM may function to more easily receive electrons from the organic semiconductor material to thus create a hole-doping effect, thereby further increasing electron injection performance, resulting in increased charge mobility.

In Formulas 1 and 2, $R_1$ and $R_2$ may be methyl and isopropyl, respectively, among the alkyl group.

For example, examples of the precursor compound represented by Formulas 1 and 2 may include, but are not limited to, compounds represented by Formulas 3 to 13 below:

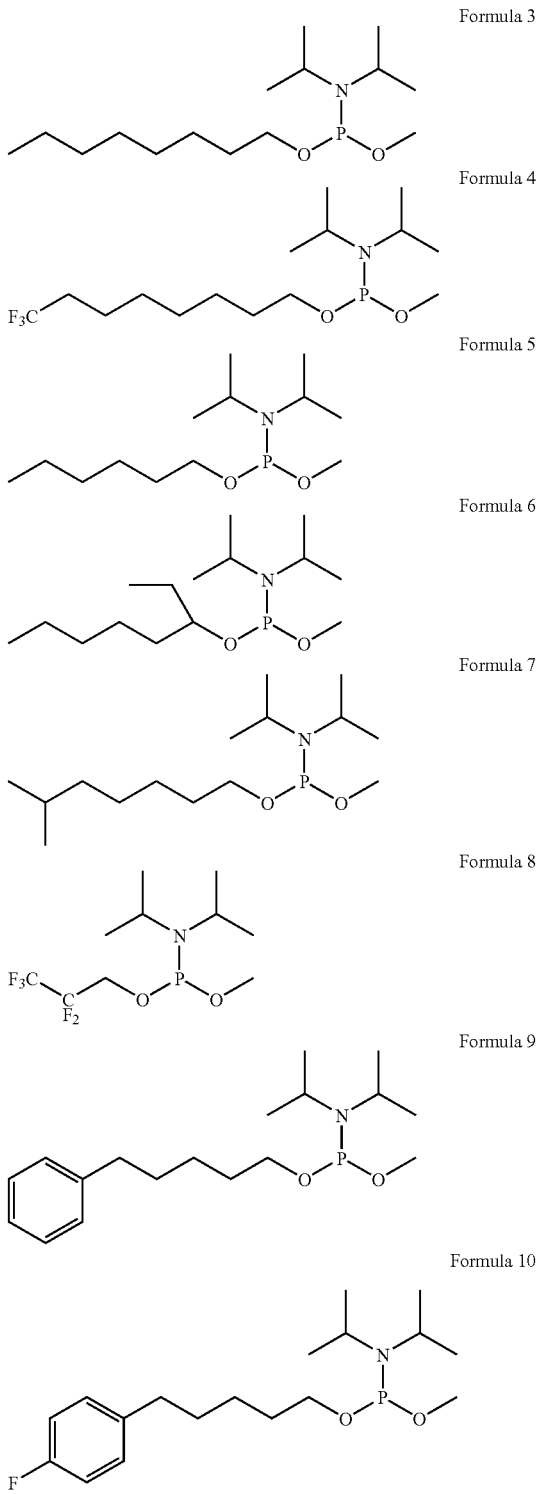

-continued

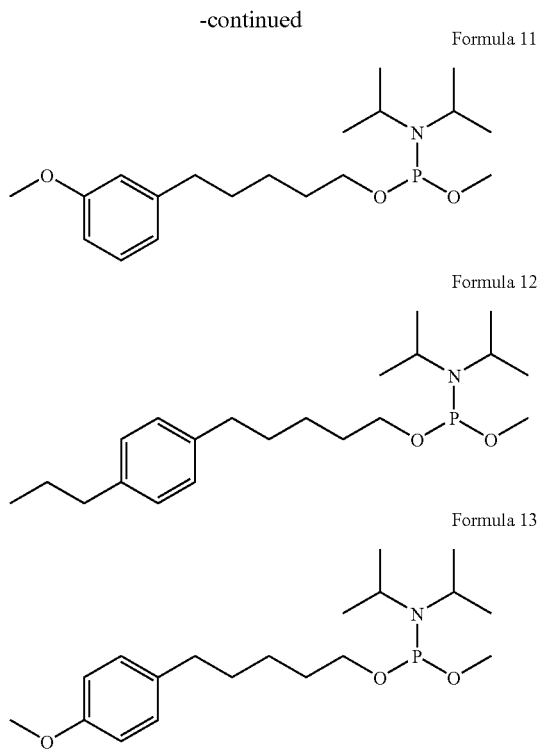

Formula 11

Formula 12

Formula 13

The precursor compound represented by Formulas 1 and 2 may be synthesized using a typical synthesis process, but example embodiments may not be limited thereto. The synthesis process may be represented by Reaction 1 below:

Reaction 1

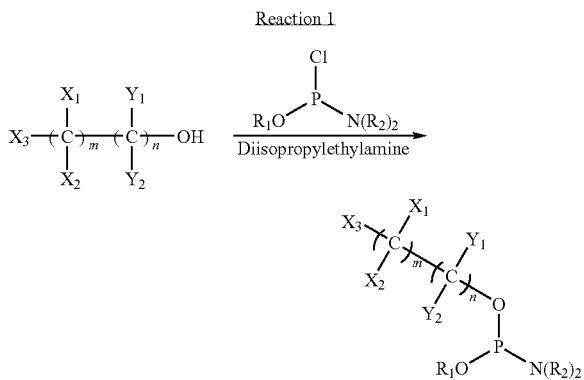

wherein $R_1$ and $R_2$ are each independently a $C_{1-30}$ alkyl group, $R_1$ and $R_2$ being substitutable with one or more selected from among a cyano group, an alkoxy group, and a $C_{6-12}$ aryl group, $X_1$, $X_2$, $X_3$, $Y_1$ and $Y_2$ are each independently hydrogen, fluorine, a $C_{1-12}$ alkyl group, a $C_{6-30}$ aromatic group, or a $C_{2-30}$ heteroaromatic group containing one or more heterogeneous atoms, the aromatic group or heteroaromatic group being substitutable with one or more selected from among a $C_{1-12}$ alkyl group, an alkoxy group, an ester group, a carboxyl group, a thiol group, and an amine group, and m is an integer from about 0 to about 50, and n is an integer from about 1 to about 50.

The reaction may be performed at ambient temperature or at about 10° C.~about 180° C. for about 1 hours~about 24 hours using a general organic solvent in a nitrogen or hydrogen atmosphere, and a typical purification process, e.g. chromatography, a filtration process, and a concentration process may be further conducted.

The thickness of the SAM of example embodiments may be appropriately determined according to the choice of those skilled in the art, and may fall in a range from about ones to about hundreds of Å, but example embodiments may not be limited thereto.

As the source/drain electrodes on which the SAM is formed, any material may be used without limitation as long as it provides an —OH functional group able to form a single bond with the phosphate group of the SAM. For example, oxide or oxide film-containing material may be used, and examples thereof may include, but may not be limited to, metal oxide or a conductive polymer coated with an oxide film.

As the metal oxide, any material may be used as long as it is known in the art, including indium tin oxide (ITO) or indium zinc oxide (IZO).

The source/drain electrodes may have a thickness from about 500 Å to about 2,000 Å, and may be patterned through a typical process, e.g., photolithography.

In the OTFT of example embodiments, any substrate may be used without limitation as long as it is known in the art, and examples thereof may include, but may not be limited to, silica, glass, and plastic, which may be appropriately used according to the choice of those skilled in the art, in consideration of the end use. Examples of the plastic substrate may include, but may not be limited to, polyethylene naphthalate, polyethylene terephthalate, polycarbonate, polyvinylalcohol, polyacrylate, polyimide, polynorbonene, and polyethersulfone. The substrate may be patterned through a typical process.

The gate electrode included in the OTFT of example embodiments may be formed using a typical material without limitation. Useful are one or more selected from among metals including gold (Au), silver (Ag), aluminum (Al), nickel (Ni), molybdenum (Mo), tungsten (W), and chromium (Cr), or alloys thereof (e.g., Mo/W alloy), metal oxides including indium tin oxide (ITO) and indium zinc oxide (IZO), and conductive polymers, including polythiophene, polyaniline, polyacetylene, polypyrrole, polyphenylene vinylene, and a mixture of PEDOT (polyethylenedioxythiophene) and PSS (polystyrenesulfonate). The gate electrode may have a thickness from about 500 Å to about 2,000 Å, and may be patterned through a typical process.

The gate insulating layer included in the OTFT of example embodiments may be formed using a typical insulator having a high-k dielectric constant. For example, a ferroelectric insulator, an inorganic insulator and/or an organic insulator may be used, but example embodiments may not be limited thereto.

For example, a ferroelectric insulator selected from among $Ba_{0.33}Sr_{0.66}TiO_3$ (BST), $Al_2O_3$, $Ta_2O_5$, $La_2O_5$, $Y_2O_3$ and $TiO_2$, an inorganic insulator selected from among $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $Bi_4Ti_3O_{12}$, $SiO_2$, $SiN_x$ and AlON, or an organic insulator selected from among polyimide, benzocyclobutene (BCB), parylene, polyacrylate, polyvinyl alcohol, and polyvinyl phenol. For example, an insulator containing a crosslinking agent, or an organic-inorganic hybrid type insulator, may be used. The gate insulating layer may have a thickness from about 1,000 Å to about 10,000 Å, but example embodiments may not be limited thereto. Further, the gate insulating layer may be patterned through a typical process.

As the organic semiconductor layer included in the OTFT of example embodiments, any organic semiconductor material may be used without limitation as long as it is known in the art. For example, the semiconductor material may include one or more selected from the group consisting of known low-molecular-weight or oligomer organic semiconductor materials and known polymer organic semiconductor materials, which may be appropriately used according to the choice of those skilled in the art.

For example, anthracene, tetracene, pentacene, oligothiophene, polythiophene, merocyanine, copper phthalocyanine, perylene, polyaniline, polyacetylene, polypyrrole, polyphenylene, rubrene, coronene, anthradithiophene, polyfluorene, polyphenylenevinylene, polythienylthiazole, and derivatives thereof may be used alone or in combinations of two or more, but example embodiments may not be limited thereto. The semiconductor layer may have a thickness from about 300 Å to about 2,000 Å, and may be patterned through a typical process.

Figure 2:
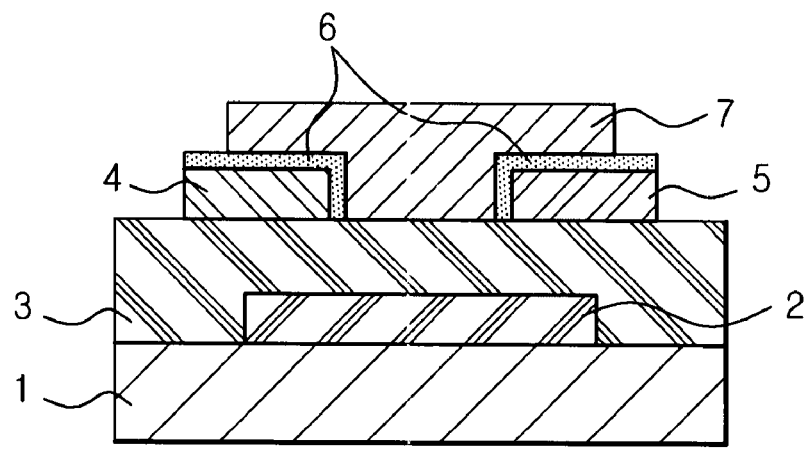

The OTFT of example embodiments may have a bottom contact structure or a top gate structure. As illustrated in FIG. 2, the OTFT of example embodiments may have a bottom contact structure, including a substrate 1, a gate electrode 2 positioned on the substrate, a gate insulating layer 3 positioned on the gate electrode, source/drain electrodes 4, 5 positioned on the gate insulating layer, an SAM 6 positioned on the source/drain electrodes, and an organic semiconductor layer 7 positioned on the SAM and the gate insulating layer.

Figure 3:
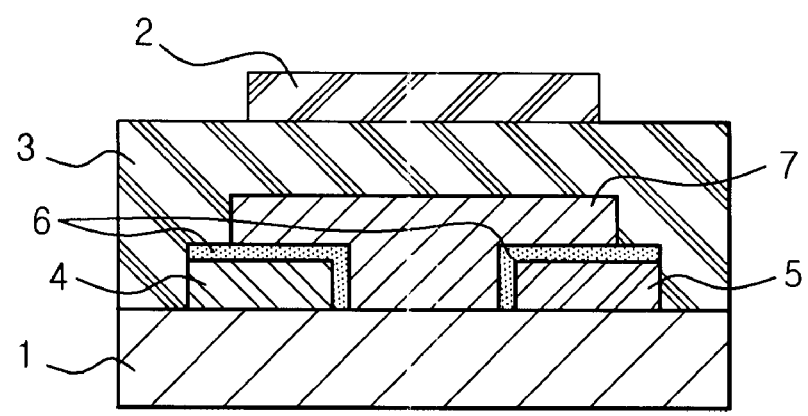

In addition, as illustrated in FIG. 3, the organic electronic device of example embodiments may have a top gate structure, including a substrate 1, source/drain electrodes 4, 5 positioned on the substrate, an SAM 6 positioned on the source/drain electrodes, an organic semiconductor layer 7 positioned on the SAM and the substrate, a gate insulating layer 3 positioned on the semiconductor layer, and a gate electrode 2 positioned on the gate insulating layer. However, example embodiments may not be limited to such a structure, and the structure may be modified within a range that does not inhibit the purpose of example embodiments.

The OTFT of example embodiments may include a more stable single bond type phosphate-based SAM without intermolecular cross-linking, between the source/drain electrodes and the organic semiconductor layer. Thereby, contact resistance between the source/drain electrodes and the organic semiconductor layer may be decreased, and as well, electron injection performance may be improved, thus exhibiting improved electrical properties, e.g., increased charge mobility. Accordingly, the OTFT of example embodiments may be effectively applied to various display devices. Examples of the display device may include, but may not be limited to, liquid crystal displays, plasma displays, field emission displays, light emitting diodes, and organic EL displays.

In addition, example embodiments provide a method of manufacturing the OTFT mentioned above. For example, the OTFT manufacturing method according to example embodiments may include forming a gate electrode on a substrate, forming a gate insulating layer on the gate electrode, forming source/drain electrodes on the gate insulating layer, forming a single bond type phosphate-based SAM without intermolecular crosslinking, on the source/drain electrodes, and forming an organic semiconductor layer on the SAM and the gate insulating layer.

The OTFT manufacturing method according to example embodiments may include forming source/drain electrodes on a substrate, forming a single bond type phosphate-based SAM without intermolecular crosslinking, on the source/drain electrodes, forming an organic semiconductor layer on the SAM and the substrate, forming a gate insulating layer on the organic semiconductor layer, and forming a gate electrode on the gate insulating layer.

Through the manufacturing method according to example embodiments, the OTFT having the bottom contact structure illustrated in FIG. 2 may be obtained, and through the manufacturing method according to other example embodiments, the OTFT having the top gate structure illustrated in FIG. 3 may be obtained.

As such, the formation of the SAM may be performed by immersing the surface of the source/drain electrodes in a mixture of a solution including a precursor compound for SAM and a solvent, and a catalyst, and further immersing the surface of the source/drain electrodes in a mixture of an organic solvent, amine, and water containing an oxidant. Further, annealing the surface of the immersed source/drain electrodes may be selectively performed.

Below, the manufacturing method of example embodiments may be stepwisely described in detail. The following procedure may be based on the method of manufacturing a bottom contact type OTFT, but the manufacturing method of example embodiments may also be applied to a top gate type OTFT.

A substrate may be washed through a typical process to remove impurities, and then a gate electrode may be formed through deposition and patterning. As such, the materials for the substrate and the gate electrode are as mentioned above.

When the gate electrode is formed on the substrate, a gate insulating layer may be formed on the gate electrode through a typical process. The material for the gate insulating layer may be as mentioned above, and examples of the formation process may include, but may not be limited to, solution processes, e.g., thermal evaporation, vacuum deposition, spin coating and/or printing. Further, soft baking may be performed at about 40° C.~about 100° C. for about 1 min~about 30 min and then hard baking may be performed at about 100° C.~about 200° C. for about 0.5 hours~about 3 hours, if necessary.

When the gate insulating layer is formed, source/drain electrodes may be formed thereon. For example, a thin film may be formed on the gate insulating layer using source/drain electrode material through a typical thin film formation process, and may then be subjected to typical exposure and development to expose the region for source/drain electrodes (or regions other than source/drain electrodes). Subsequently, the thin film may be etched using acetonitrile through a typical process, and finally a photoresist may be removed using a photoresist stripper, thus forming the source/drain electrodes.

As such, the materials for source/drain electrodes may be as mentioned above, and may include metal oxide, e.g., ITO and/or IZO. Also, examples of the thin film formation process for forming the source/drain electrodes on the gate insulating layer may include, but may not be limited to, thermal evaporation, spin coating, roll coating, spray coating and/or printing.

When the source/drain electrodes are formed, the surface of the electrode may be treated with a precursor compound capable of forming a single bond type phosphate-based SAM without intermolecular crosslinking, thus forming the SAM on the source/drain electrodes. As such, the descriptions of the SAM and the precursor compound therefor may be as given above, and may be omitted herein.

For example, this step may be performed by immersing the surface of the source/drain electrodes in a mixture of a solution including the precursor compound for SAM and a solvent, and a catalyst, and further immersing the surface of the source/drain electrodes in a mixture of an organic solvent, amine and water, containing an oxidant. Further, annealing the surface of the immersed source/drain electrodes may be selectively performed.

These processes are as follows. The surface of the source/drain electrodes may be immersed in the mixture of the solution including the precursor compound for SAM, the solvent, and the catalyst. This process may function to convert the phosphoramidite functional groups contained in the precursor compound into phosphite functional groups through reaction with the —OH groups exposed to the surface of the source/drain electrodes at a ratio of about 1:1, therefore forming single bonds to the surface of source/drain electrodes (FIG. 1).

As the solvent, a general organic solvent, water, or a mixture thereof may be used without limitation, and examples thereof may include, but may not be limited to, ketones, including acetone, methylethylketone, and methylisobutylketone, glycol ethers, including ethyleneglycol dimethyl ether and triethyleneglycol diethyl ether, glycol ether acetates, including propyleneglycol monomethyl ether acetate (PGMEA), acetates, including ethyl acetate, butoxyethoxy ethyl acetate, butyl carbitol acetate (BCA), and dihydroterpineol acetate (DHTA), terpineols, trimethyl pentanediol monoisobutyrate (TEXANOL), dichloroethene (DCE), chlorobenzene, and N-methyl-2-pyrrolidone (NMP), which may be used alone or in combinations of two or more.

The concentration of the precursor compound in the solution including the precursor compound and the solvent may be appropriately determined according to the choice of those skilled in the art, and may range from about 1 mM to about 100 mM in consideration of the extent of modification of the surface of the source/drain electrodes and the decrease in contact resistance.

As the catalyst, any acidic material may be used without limitation as long as it is known in the art, and specific examples thereof may include, but may not be limited to, a tetrazole solution, HCl, phosphoric acid and/or sulfuric acid, for example, a tetrazole solution in which tetrazole is contained in a tetrahydrofuran solvent in a concentration of about 0.1 mM~about 100 mM.

The mixing ratio of the solution including the precursor compound and the solvent, and the catalyst may be appropriately selected by those skilled in the art, in consideration of the end use and the type of precursor compound, and the solution including the precursor compound and the solvent may be mixed with the catalyst at a volume ratio of about 1:1 to about 100:1. Although this process is not particularly limited, it may be performed at about 10° C.~about 100° C. for a period of time from about 10 sec to about 1 hour, for example, at room temperature for a period of time from about 30 sec to about 5 min.

Subsequently, the surface of the source/drain electrodes may be further immersed in the mixture of an organic solvent, amine and water, containing an oxidant. This process may function to ensure that the phosphite functional groups bound to the surface of the source/drain electrodes may not be crosslinked with each other but may be oxidized to thus be converted into phosphate functional groups (FIG. 1).

As the oxidant, known oxidants may be used without limitation. Iodine, tert-BuOOH, Beaucage reagent and/or $S_8/CS_2$/Pyr/$Et_3$N may be used. The amount of oxidant may be appropriately determined according to the choice of those skilled in the art, and may be about 0.001 M~about 10 M, for example, about 0.01 M~about 1 M.

As the organic solvent contained in the mixture, a general organic solvent may be used. As the amine, known amines may be used without limitation. The mixing ratio of organic solvent, amine, and water may be appropriately determined according to the choice of those skilled in the art, in consideration of reactivity. The mixture of tetrahydrofuran, pyridine, and water at a volume ratio from about 10:10:10 to about 70:20:10 may be used, but example embodiments may not be limited thereto. Further, iodine may be used as the oxidant, and a mixture of tetrahydrofuran, pyridine and water be used.

Although this process is not particularly limited, it may be performed at about 10° C.~about 100° C. for a period of time from about 10 sec to about 1 hour, for example, at room temperature for a period of time from about 30 sec to about 5 min.

Annealing of the surface of the immersed source/drain electrodes may be further performed. When performing the annealing following the surface treatment of the source/drain electrodes, the adhesion of the source/drain electrodes may be increased to thus further increase charge mobility. The annealing process may be typically performed without limitation, and may be performed at about 50° C.~about 200° C. for about 1 min to about 2 hours.

Finally, on the SAM and the gate insulating layer, an organic semiconductor material may be applied through a typical coating process, thus forming an organic semiconductor layer. This organic semiconductor material may be as mentioned above, and examples of the formation process thereof may include, but may not be limited to, thermal evaporation, screen printing, printing, spin coating, dip coating and/or imprinting.

The method of manufacturing the OTFT according to example embodiments may further include subjecting the surface of the source/drain electrodes to acid treatment or UV ozone treatment between forming source/drain electrodes on the gate insulating layer and forming a single bond type phosphate-based SAM without intermolecular crosslinking, on the source/drain electrodes or between forming source/drain electrodes on a substrate and forming a single bond type phosphate-based SAM without intermolecular crosslinking, on the source/drain electrodes.

Before surface treatment of the source/drain electrodes with the SAM, acid treatment or UV ozone treatment may be performed, such that the surface of the source/drain electrodes may become hydrophilic so as to further increase the surface adhesion of the phosphate functional group.

The acid treatment may be performed through a typical process known in the art, and may be performed by immersing the surface of the source/drain electrodes in a solution of an organic acid and/or an inorganic acid at about 15° C.~about 35° C. for about 0.5 sec~about 30 sec.

As the organic acid, a solution of acid represented by Formula 14 below may be used, but example embodiments may not be limited thereto:

 $R_3COOH$ Formula 14 wherein $R_3$ is a $C_{1-12}$ alkyl group, an alkenyl group, an alkynyl group, a $C_{3-30}$ cycloalkyl group, a $C_{6-30}$ aryl group, or a fluoro-substituted functional group thereof.

Examples of the inorganic acid may include, but may not be limited to, HI, HBr, HCl, HF, $HNO_3$, $H_3PO_4$, $H_2SO_4$ and/or mixtures thereof. As the mixture, an ITO etchant including HCl or $HNO_3$ may be used.

The UV ozone treatment is performed through a typical process known in the art, and may be performed by irradiating the surface of the source/drain electrodes at a wavelength of about 240 nm~about 270 nm using a lamp having power of about 0.2~0.5 W/cm³ for about 1 min~about 30 min, but example embodiments may not be limited thereto.

A better understanding of example embodiments may be obtained in light of the following examples which are set forth to illustrate, but are not to be construed to limit example embodiments.

[Synthesis of Precursor Compound]

Synthesis Example 1

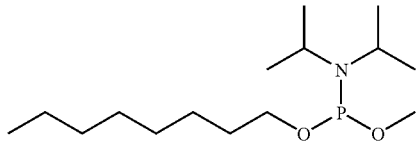

A mixture solution including methylene chloride (about 10 ml) and 1-octanol (about 0.26 g, about 2.0 mmol) was added with diisopropylethylamine (about 0.56 ml, about 3.21 mmol), and then treated with N,N-diisopropylmethyl-phosphonamidic chloride (about 0.45 g, about 2.27 mmol) at about room temperature for about 2 hours. Subsequently, the reaction mixture was diluted with methylene chloride (about 20 ml), and the resultant organic film was washed with NaHCO₃ saturated solution, water, and brine, in that order. The washed organic film was dried using sodium sulfate and then concentrated in a vacuum. The organic residue thus obtained was purified through silica gel chromatography using hexane as an eluent, yielding the precursor compound 1 of the above formula.

$^{31}$P NMR (CDCl₃) 148; $^{1}$H NMR (CDCl₃) 3.75–3.45 (m, 4H), 3.38 (d, 3H), 1.62–1.57 (m, 2H), 1.43–1.27 (m, 10H), 1.15 (d, 12H), 0.96 (t, 3H).

Synthesis Example 2

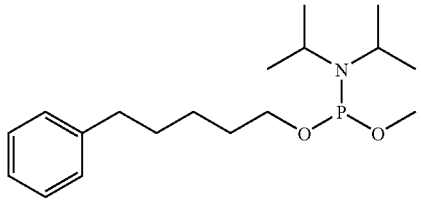

Into a flask containing magnesium turnings (about 750 mg, about 31 mmol), ether (about 10 ml) was added, and then a small amount of iodine (about 1 mg~about 5 mg) was added, and the resulting mixture was stirred for several min until it was colorless. Bromobenzene (about 100 ml, about 0.9 mmol) was added to the mixture and then heated to thus initiate the reaction. While the mixture was weakly refluxed, a mixture solution of bromobenzene (about 3.2 ml, about 30 mmol) and ether (about 50 ml) was added in droplets thereto for about 2.5 hours. The deeply browned mixture was stirred at ambient temperature for about 3 hours in a nitrogen atmosphere and then cooled in an ice-salt bath at about −5° C. To the mixture, a mixture solution of 5-benzyloxy-1-bromopentane (about 1.54 g, about 6 mmol) and ether (about 10 ml) was added in droplets. The resulting mixture was stirred for about 2 hours, cooled, heated to reflux for about 3 hours, and then cooled at ambient temperature. The above solution was poured onto ice water while being stirred, and hydrochloric acid (about 1 N) was added in droplets thereto. The pH thereof was maintained at about 4. The film was separated, after which the water-soluble film was extracted three times with methylene chloride. The organic layer was dried using MgSO₄, filtered and concentrated to thus obtain brown oil, which was then subjected to column chromatography, yielding 5-phenylpentyl benzyl ether. A mixture of 5-phenylpentyl benzyl ether and methanol (about 50 ml) was blended with about 10% Pd/C catalyst, stirred for about 3 hours in a hydrogen atmosphere, and then filtered through a Celite pad. The filtrate was concentrated, thus obtaining 5-phenylpentylalcohol. Using 5-phenylpentylalcohol as a starting material, the same procedure as in Example 1 was performed, thereby obtaining the precursor compound 2 of the above formula.

$^{31}$P NMR (CDCl₃) 146; $^{1}$H NMR (CDCl₃) 7.32–7.17 (m, 5H), 3.56–3.47 (t, 2H), 3.41 (s, 3H), 3.02–2.94 (m, 2H), 2.65–2.54 (t, 2H), 1.52–1.24 (m, 6H), 1.13 (d, 12H)

[Manufacture of Organic Thin Film Transistor]

EXAMPLE 1

On a washed glass substrate, a gate electrode was formed to a thickness of about 1500 Å through sputtering using aluminum. Subsequently, a silanol-based organic-inorganic hybrid type insulator was applied to a thickness of about 7000 Å on the gate electrode through spin coating at about 2000 rpm to thus form a gate insulating layer, after which soft baking at about 70° C. for about 10 min and then hard baking at about 150° C. for about 90 min were performed, thus forming an insulating layer. Further, ITO was deposited to a thickness of about 1000 Å thereon through thermal evaporation under a vacuum condition (about 2×10⁻⁷ torr, substrate temperature of about 50° C., and deposition rate of about 0.85 Å/sec), followed by photolithography to thus form an ITO electrode pattern.

Thereafter, a precursor solution, in which the precursor compound obtained in Synthesis Example 1 was dissolved to about 10 mM in ethylalcohol, was mixed with a tetrazole solution, in which tetrazole was dissolved to about 10 mM in tetrahydrofuran, at a volume ratio of about 10:1 to obtain a mixture, in which the ITO electrode was then immersed at room temperature for about 1 min and washed with tetrahydrofuran. The electrode was further immersed at room temperature for about 1 min in a solution in which iodine was dissolved to about 0.05 M in a mixture of tetrahydrofuran, pyridine and water (at a volume ratio of tetrahydrofuran:pyridine:water=about 70:20:10), and was then washed with tetrahydrofuran, thereby forming a phosphate-based SAM. Furthermore, a solution in which polyhexylthiophene was dissolved to about 0.1 wt % in dichlorobenzene was applied on the SAM through spin coating at about 1000 rpm to thus form a semiconductor layer about 500 Å thick, which was then thermally treated at about 100° C. for about 15 min, thereby manufacturing an OTFT.

EXAMPLE 2

An OTFT was manufactured in the same manner as in Example 1, with the exception that the precursor compound obtained in Synthesis Example 2 was used instead of the precursor compound obtained in Synthesis Example 1.

EXAMPLE 3

An OTFT was manufactured in the same manner as in Example 1, with the exception that the surface of the ITO electrode was subjected to acid treatment using an ITO etchant at about room temperature for about 10 sec, before the formation of the SAM on the ITO electrode.

EXAMPLE 4

An OTFT was manufactured in the same manner as in Example 1, with the exception that the surface of the ITO electrode was subjected to UV ozone treatment at a wavelength of about 254 nm using a lamp having a power of about 0.28 W/cm$^3$ for about 5 min, before the formation of the SAM on the ITO electrode.

EXAMPLE 5

An OTFT was manufactured in the same manner as in Example 1, with the exception that the annealing process was performed at about 120° C. for about 15 min after forming the SAM on the ITO electrode.

EXAMPLE 6

An OTFT was manufactured in the same manner as in Example 3, with the exception that the annealing process was performed at about 100° C. for about 30 min, after forming the SAM on the ITO electrode.

COMPARATIVE EXAMPLE 1

An OTFT was manufactured in the same manner as in Example 1, with the exception that the SAM was not formed on the ITO electrode.

COMPARATIVE EXAMPLE 2

An OTFT was manufactured in the same manner as in Example 6, with the exception that the SAM was not formed on the ITO electrode.

[Evaluation of Properties of OTFT]

Figure 4:
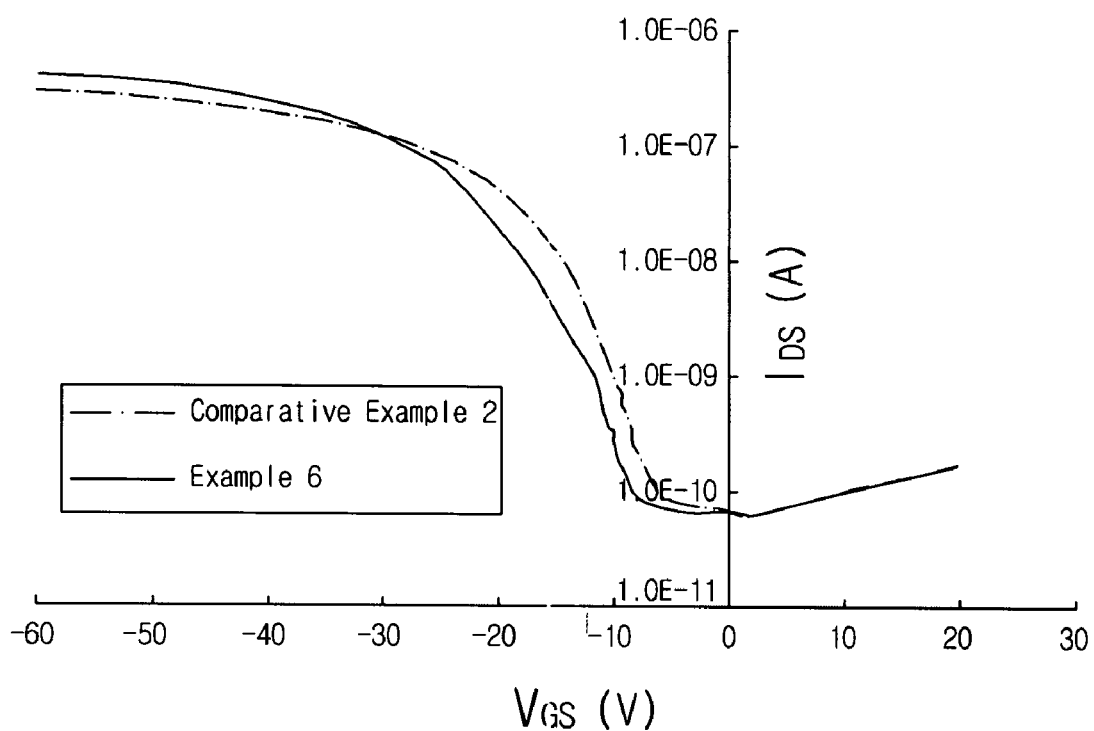

In order to evaluate the electrical properties of OTFTs manufactured in Example 6 and Comparative Example 2, current transfer properties were measured using a semiconductor analyzer (4200-SCS), available from KEITHLEY. The results are shown in FIG. 4. As is apparent from FIG. 4, the OTFT of Example 6 may have higher charge mobility than the OTFT of Comparative Example 2.

The charge mobility of OTFTs manufactured in Examples 1 to 6 and Comparative Examples 1 and 2 was calculated using the following current equation for the saturation region. For example, the current equation for the saturation region was converted into a graph of $(I_{SD})^{1/2}$ to $V_G$, and the charge mobility was calculated from the slope of the converted graph:

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

wherein $I_{SD}$ is source-drain current, $\mu$ or $\mu_{FET}$ is charge mobility, $C_o$ is oxide film capacitance, W is the channel width, L is the channel length, $V_G$ is the gate voltage, and $V_T$ is the threshold voltage.

The results are given in Table 1 below.

TABLE 1

| No. | Charge Mobility (cm$^2$/Vs) |
|---|---|
| Ex. 1 | 0.0080 |
| Ex. 2 | 0.0164 |
| Ex. 3 | 0.0109 |
| Ex. 4 | 0.0086 |
| Ex. 5 | 0.065 |
| Ex. 6 | 0.0223 |
| C. Ex. 1 | 0.0010 |
| C. Ex. 2 | 0.0015 |

From the results of Table 1, the OTFT of example embodiments may have improved electrical properties, e.g., charge mobility.

As described hereinbefore, example embodiments provide an OTFT including a phosphate-based SAM and a method of manufacturing the same. According to example embodiments, a more stable single bond type phosphate-based SAM without intermolecular cross-linking may be provided between source/drain electrodes and an organic semiconductor layer, thus decreasing contact resistance between the source/drain electrodes and the organic semiconductor layer. Further, the work function of material for the source/drain electrodes may be higher than that of material for the organic semiconductor layer, thereby providing an OTFT having improved electrical properties, e.g., increased charge mobility.

Although example embodiments have been disclosed for illustrative purposes, those skilled in the art will appreciate that various modifications, additions and substitutions are possible, without departing from the scope and spirit of the accompanying claims.

What is claimed is:

1. An organic thin film transistor, comprising a substrate; a gate electrode; a gate insulating layer; source/drain electrodes having functional groups exposed on a surface thereof; an organic semiconductor layer; and a single bond type phosphate-based self-assembled monolayer without intermolecular crosslinking, wherein individual molecules constituting the self-assembled monolayer are not crosslinked with each other, each of the individual molecules of the self-assembled monolayer forming a single bond with each functional group on the surface of the source/drain electrodes, and wherein the self-assembled monolayer has —PO$_3$R$_1$(R) groups, in which each R is a C$_{1-30}$ alkyl group, R being substitutable with one or more selected from among fluorine, an alkoxy group and a C$_{6-12}$ aryl group, and R$_1$ is a C$_{1-30}$ alkyl group, R$_1$ being substitutable with one or more selected from among a cyano group, an alkoxy group, and a C$_{6-12}$ aryl group.

2. The transistor as set forth in claim 1, wherein the self-assembled monolayer is formed from a precursor compound represented by Formula 1 or 2 below:

Formula 1

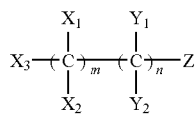

wherein Z is OPN(R$_2$)$_2$OR$_1$, in which R$_1$ and R$_2$ are each independently a C$_{1-30}$ alkyl group, R$_1$ and R$_2$ being substitutable with one or more selected from among a cyano group, an alkoxy group, and a C$_{6-12}$ aryl group, X$_1$, X$_2$, X$_3$, Y$_1$ and Y$_2$ are each independently hydrogen, fluorine, a C$_{1-12}$ alkyl group, a C$_{6-30}$ aromatic group, or a C$_{2-30}$ heteroaromatic group containing one or more heterogeneous atoms, the aromatic group or heteroaromatic group being substitutable with one or more selected from among a C$_{1-12}$ alkyl group, an alkoxy group, an ester group, a carboxyl group, a thiol group, and an amine group, and m is an integer from about 0 to about 50, and n is an integer from about 1 to about 50; and Formula 2

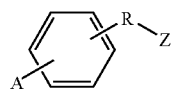

wherein Z is OPN(R$_2$)$_2$OR$_1$, in which R$_1$ and R$_2$ are each independently a C$_{1-30}$ alkyl group, R$_1$ and R$_2$ being substitutable with one or more selected from among an alkoxy group, and a C$_{6-12}$ aryl group, A is hydrogen, fluorine, an alkoxy group, a C$_{6-30}$ aromatic group, or a C$_{2-30}$ heteroaromatic group containing one or more heterogeneous atoms, the aromatic group or heteroaromatic group being substitutable with one or more selected from among a C$_{1-12}$ alkyl group, an alkoxy group, an ester group, a carboxyl group, a thiol group, and an amine group, and the C$_{1-12}$ alkyl group being substitutable with one or more selected from among fluorine, an alkoxy group, an ester group, a carboxyl group, a thiol group, and an amine group, and R is a C$_{1-30}$ alkyl group, which is substitutable with one or more selected from among a cyano group, an alkoxy group, and a C$_{6-12}$ aryl group.

3. The transistor as set forth in claim 2, wherein at least one among the X$_1$, X$_2$, X$_3$, Y$_1$ and Y$_2$ is substituted with one or more fluorine atoms, and the A is substituted with one or more fluorine atoms.

4. The transistor as set forth in claim 2, wherein the R$_1$ is methyl and the R$_2$ is isopropyl.

5. The transistor as set forth in claim 2, wherein the precursor compound represented by Formula 1 or 2 is selected from the group consisting of compounds represented by Formulas 3 to 13 below:

Formula 3

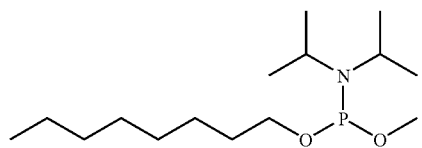

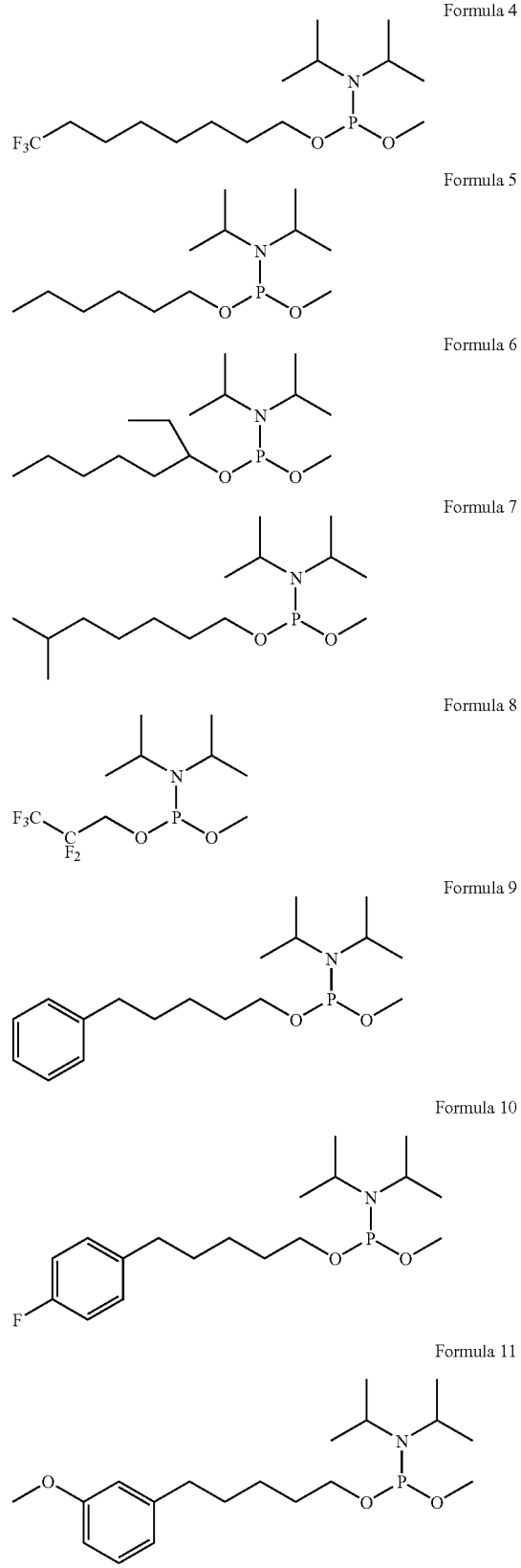

-continued

Formula 12

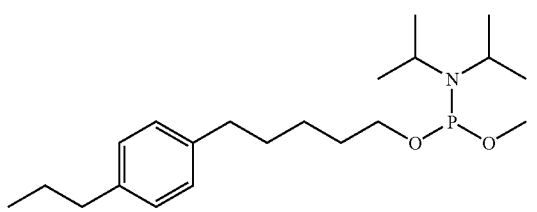

Formula 13

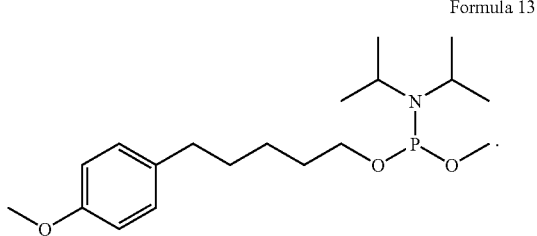

6. The transistor as set forth in claim 1, wherein the self-assembled monolayer has a thickness from about ones to about hundreds of Å.

7. The transistor as set forth in claim 1, wherein the source/drain electrodes comprise a material able to provide an —OH functional group.

8. The transistor as set forth in claim 7, wherein the source/drain electrodes comprise metal oxide or a conductive polymer coated with an oxide film.

9. The transistor as set forth in claim 1, which has a bottom contact structure or a top gate structure.

* * * * *